United States Patent
Perriat et al.

(10) Patent No.: US 8,357,545 B2
(45) Date of Patent: Jan. 22, 2013

(54) HYBRID NANOPARTICLES WITH LN$_2$O$_3$ CORE AND CARRYING BIOLOGICAL LIGANDS, AND METHOD OF PREPARATION THEREOF

(75) Inventors: Pascal Perriat, Lyons (FR); Cédric Louis, Les Cotes d'Arey (FR); Christophe Marquette, Lyons (FR); Rana Bazzi, Villeurbanne (FR); Stéphane Roux, Pont de Cheruy (FR); Olivier Tillement, Fontaine Saint Martin (FR); Gilles Ledoux, Lyons (FR)

(73) Assignees: Universite Claud Bernard Lyon I, Villeurbanne Cedex (FR); Centre National de la Recherche Scientifique (C.N.R.S.), Paris Cedex (FR); Institut National des Sciences Appliquees de Lyon, Villeurbanne Cedex (FR)

( * ) Notice: Subject to any disclaimer, the term of this patent is extended or adjusted under 35 U.S.C. 154(b) by 943 days.

(21) Appl. No.: 10/591,465

(22) PCT Filed: Mar. 2, 2005

(86) PCT No.: PCT/FR2005/000491
§ 371 (c)(1),
(2), (4) Date: Jun. 29, 2007

(87) PCT Pub. No.: WO2005/088314
PCT Pub. Date: Sep. 22, 2005

(65) Prior Publication Data
US 2007/0281324 A1    Dec. 6, 2007

(30) Foreign Application Priority Data
Mar. 2, 2004 (FR) .................................... 04 02115

(51) Int. Cl.
*G01N 33/553* (2006.01)

(52) U.S. Cl. ....................................................... 436/525
(58) Field of Classification Search ................... 436/525
See application file for complete search history.

(56) References Cited

U.S. PATENT DOCUMENTS

| | | | | | |
|---|---|---|---|---|---|
| 4,921,589 | A | * | 5/1990 | Yates et al. | 204/157.5 |
| 5,427,767 | A | * | 6/1995 | Kresse et al. | 424/9.32 |

(Continued)

FOREIGN PATENT DOCUMENTS

| FR | 2867180 | 9/2005 |
|---|---|---|
| FR | 2877571 | 5/2006 |

(Continued)

OTHER PUBLICATIONS

Molina et al. "Structure and Luminescence of Eu3+ doped class I Siloxane-poly(ehtylene glycol) hybrids" Chem. Mater. 2001, 13, 2818-2813.*

(Continued)

*Primary Examiner* — Mark Shibuya
*Assistant Examiner* — Pensee Do
(74) *Attorney, Agent, or Firm* — Clark & Brody (57) ABSTRACT

The invention concerns hybrid nanoparticles containing:
a nanosphere, of mean diameter included in the range from 2 to 9 nm, of which at least 90% by weight consists of Ln$_2$O$_3$ where Ln represents a rare earth, optionally doped with a rare earth or an actinide, or a mixture of rare earths, or a rare earth and actinide mixture, in which at least 50% of the metal ions are rare earth ions,
a coating around the nanosphere chiefly consisting of functionalized polysiloxane, having a mean thickness included in the range from 0.5 to 10 nm, preferably greater than 2 nm and no more than 10 nm, and
at least one biological ligand grafted by covalent bonding to the polysiloxane coating
and their method of preparation.

31 Claims, 7 Drawing Sheets

U.S. PATENT DOCUMENTS

| | | | |
|---|---|---|---|
| 6,099,964 A * | 8/2000 | Baumann et al. | 428/402 |
| 6,368,586 B1 | 4/2002 | Jacob et al. | |
| 6,955,639 B2 | 10/2005 | Hainfeld et al. | |
| 7,101,719 B2 * | 9/2006 | O'Beirne et al. | 436/545 |
| 2002/0006632 A1 * | 1/2002 | Ponnampalam et al. | 435/7.92 |
| 2003/0180780 A1 | 9/2003 | Feng et al. | |
| 2004/0075083 A1 * | 4/2004 | Li et al. | 252/301.4 R |
| 2009/0169892 A1 * | 7/2009 | Bazzi et al. | 428/404 |

FOREIGN PATENT DOCUMENTS

| | | |
|---|---|---|
| WO | WO 00/17642 | 3/2000 |
| WO | WO 00/29617 | 5/2000 |
| WO | 03/080743 | 10/2003 |
| WO | 2004/112590 | 12/2004 |
| WO | 2005/088314 | 9/2005 |
| WO | 2005/120590 | 12/2005 |
| WO | 2006/012201 | 2/2006 |

OTHER PUBLICATIONS

C. Louis et al., "Nanosized Hybrid Particles with Double Luminescence for Biological Labeling", Chem. Mater. 2005, 17, 1673-1682.

J. Feng et al., "Functionalized Europium Oxide Nanoparticles Used as a Fluorescent Label in an Immunoassay for Atrazine", Analytical Chemistry, vol. 75, No. 19, Oct. 1, 2003, pp. 5282-5286.

R. Bazzi et al., "Synthesis and luminescent properties of sub-5-nm lanthanide oxides nanoparticles", Journal of Luminescence 102-103 (2003) 445-450.

C. Cannas et al., "Synthis, characterization and optical spectroscopy of a $Y_2O_3$-$SiO_2$ nanocomposite doped with $Eu^{3+}$", Journal of Non-Crystalline Solids 306 (2002) 193-199.

W. Que et al., "Yellow-to-violet upconversion in neodymium oxide nanocrystal/titania/ormosil composite sol-gel thin films derived at low temperature", Journal of Applied Physics, vol. 90, No. 9, Nov. 1, 2001, pp. 4865-4867.

W. Que et al., "Fluorescence characteristics from microemulsion technique derived erbium (III) oxide nanocrystals", Materials Research Bulletin 36 (2001) 889-895.

Database Chemlabs Online, Chemical Abstracts Service, Columbus, OH, Mar. 8, 2004, B. Sun et al., "Rare earth nanoparticle for labeling biomaterial, its preparation and application" XP002300295.

M. Bruchez Jr., et al., "Semiconductor Nanocrystals as Fluorescent Biological Labels", Science, vol. 281, Sep. 25, 1998, pp. 2013-2016.

C. Feldmann, "Preparation of Nanoscale Pigment Particles", Adv. Mater. 2001, 13, No. 17, Sep. 3, 2001, pp. 1301-1303.

W. Chan et al., "Quantum Dot Bioconjugates for Ultrasensitive Nonisotopic Detection", Science, vol. 281, Sep. 25, 1998, pp. 2016-2018.

I. Hemmila, "Lanthanides as probes for time-resolved fluorometric immunoassays", Scand. J. Clin. Lab. Invest., 1988, 48, pp. 389-400.

R. Bazzi et al., "Synthesis and properties of europium-based phosphors on the nanometer scale: $Eu_2O_3$, $Gd_2O_3$:Eu, and $Y_2O_3$:Eu", Journal of Colloid and Interface Science 273 (2004), 191-197.

F. Hu et al., "Pm-149 DOTA bombesin analogs for potential radiotherapy In vivo comparison with Sm-153 and Lu-177 labeled DO3A-amide-Bala-BBN(7-14)$NH_2$", Nuclear Medicine and Biology 29 (2002) 423-430.

W. Li et al., "Development of an in vitro model for assessing the in vivo stability of lanthanide chelates", Nuclear Medicine and Biology 28 (2001) 145-154.

H. Matsudaira et al., "Iodine Contrast Medium Sensitizes Cultured Mammalian Cells to X Rays but not to y Rays", Radiation Research 84, 144-148 (1980).

I. Das et al., "Backscatter dose perturbation in kilovoltage photon beams at high atomic number interfaces[a]", Med. Phys. 22 (6), Jun. 1995, 767-773.

C. Dionet et al., "Comparisons of Carboplatin and Cisplatin as Potentiators of 5-Flourouracil and Radiotherapy in the Mouse L1210 Leukaemia Model", Anticancer Research 22: 721-726 (2002).

S. Ivy et al., "Clinical Trials With Gadolinium-Texaphyrin and Lutetium-Texaphyrin", Oncology, May 1999, 671-676.

D. Herolds et al., "Gold microspheres: a selective technique for producing biologically effective dose enhancement", Int. J. Radiat. Biol. 2000, vol. 76, No. 10, 1357-1364.

S. Cho, "Estimation of tumour dose enhancement due to gold nanoparticles during typical radiation treatments: a preliminary Monte Carlo study", Phys. Med. Biol. 50 (2005) N163-N173.

M. Engstroem et al., "High proton relaxivity for gadolinium oxide nanoparticles" Magn. Reson. Mater. Phy. (2006) 19: 180-186.

J. Bridot et al., "Hybrid Gadolinium Oxide Nanoparticles: Multimodal Contrast Agents for in Vivo Imaging", J. Am. Chem. Soc. 2007, 129, 5076-5084.

M. Flores-Gonzalez et al., "Preparing nanometer scaled Tb-doped $Y_2O_3$ luminescent powders by the polyol method", Journal of Solid State Chemistry 178 (2005)989-997.

C. Louis et al., "Synthesis and characterization of $Gd_2O_3$:$Eu^{3+}$ phosphor nanoparticles by a sol-lyophilization technique", Journal of Solid State Chemistry 173 (2003)335-341.

W. Stoeber et al., "Controlled Growth of Monodisperse Silica Spheres in the Micron Size Range[1]", Journal of Colloid and Interface Science 26, 62-69 (1968).

P. Debouttière et al., "Design of Gold Nanoparticles for Magnetic Resonance Imaging", Adv. Funct. Mater. 2006, 16, 2330-2339.

* cited by examiner

HYBRID NANOPARTICLES WITH $LN_2O_3$ CORE AND CARRYING BIOLOGICAL LIGANDS, AND METHOD OF PREPARATION THEREOF

The present invention relates to the technical area of probes for detection, tracing and quantification in biological systems. More particularly, the subject of the invention concerns novel, hybrid probe particles whose core consists of a nanoparticle containing a lanthanide sesquioxide, of mean diameter less than 10 nm, on which probe molecules are immobilized, and their method of preparation.

The use of probes associated with a labeller in biological systems for the detection (recognition) or tracing of specific substances, called targets, is a usual technique in the area of medical diagnosis and biological research. Said probes are used in particular for flow cytometry, histology, immunological assays or fluorescence microscopy, for the study of both biological materials and non-biological materials.

Usual labelling systems are, for example, radioactive isotopes of iodine, phosphorus and other elements such as the peroxidase enzyme or alkaline phosphatase whose detection requires a particular substrate. In most cases, selective coupling between the labeller and the substance to be detected is made by a single or by an association of functional molecules. Binding selectivity is essential in order to identify the target substance to be detected without any ambiguity. The reactions ensuring such coupling are known and described for example in <<Bioconjugate Techniques>>, G. T. Hermanson, Academic Press 1996 or in <<Fluorescent and Luminescent Probes for Biological Activity. A Practical Guide to Technology for Quantitative Real-Time Analysis>>, Second Edition, W. T. Mason ed., Academic Press, 1999.

Fluorescent organic dyes are very frequently used for labelling. These are fluorescein, Texas Red or Cy5 which are selectively linked to a determined biological or organic substance acting as probe. After the labelled probe is excited by an external source, most often electromagnetic, the presence of the target biological or organic substances bound to the probe is evidenced by fluorescence emission by the probe.

One of the major disadvantages of fluorescent organic dyes, at the root of current techniques, lies in their low chemical stability: they degrade, even decompose after a few million cycles of light absorption and emission in the presence of acids or radicals. Also, in most applications, they exhibit insufficient stability against incident light. In addition, fluorescent organic dyes may have phototoxic effects on the biological environment.

Fluorescent organic dyes also have the drawback of emitting over a broad spectrum range and of being excited by radiation whose wavelength lies within a very narrow bandwidth. On this account, the simultaneous identification of several substances each labelled with different fluorescent dyes, also called multiplexing, is made difficult through the overlapping of emission bands, and the counting of the differently labelled substances is limited. Also, efficient excitation of the different dyes requires several light sources, generally lasers, or the use of a complex optical assembly comprising a series of filters when white light is used as excitation source.

The prior art already proposes alternatives to the use of fluorescent organic dyes. As first alternative, it is possible to use metal complexes (chelating ligands) with a metal ion of the lanthanide group as fluorescent labeller (patents U.S. Pat. No. 4,637,988 and U.S. Pat. No. 5,891,656). The main advantage of these systems is that the excited objects have a long lifetime possibly reaching several milliseconds allowing experiments to be considered having time resolution. However, the use of these lanthanide chelates is hampered by the very high dilution of luminescence (quenching) in an aqueous medium. This considerably restricts the area of application of the chelates since biological media generally have a high water content. Attempts to separate the substance to be detected from the biological medium and to place it in an anhydrous environment have therefore been made (I. Hemmilä, Scand. J. Clin. Lab. Invest. 48, 1988, pages 389-400); however, they do not allow immunohistochemical tests since data on the point of labelling is lost during the separation step. In patents U.S. Pat. No. 4,282,382 and U.S. Pat. No. 4,259,313 it is indicated that polymer particles (latex), in which lanthanide chelates are trapped, can be used as fluorescent labellers.

Another alternative put forward in the prior art consists of labelling the probe intended to bind to the target to be detected with intrinsically luminescent particles. In particular, nanoparticles of semi-conductive material have been the subject of intense research. U.S. Pat. No. 5,990,479 and international patent applications published under numbers WO 00/17642 and WO 00/29617 show that fluorescent semiconductor nanocrystals, belonging to the elements of Group II-VI or III-V, and those which, under certain conditions consist of elements from main Group 4 of the periodic table can be used as fluorescent labeller for biological systems. On account of the phenomenon known as the <<quantum size effect>> the emission wavelength of a fluorescent semiconductor nanocrystal is determined by its size. Therefore, by causing the size of these nanocrystals to vary, a broad spectrum range can be covered from visible light to near infra-red. Their use as biological labeller is described by Warren C. W. Chan, Shuming Nie, Science, 281, 2016-2018, 1998, and by Marcel Bruichez Jr, Mario Moronne, Peter Gin, Shimon Weiss, A. Paul Alivisatos, Science, 281, 2013-2016, 1998. The preparation of semiconductor nanocrystals with a well determined emission wavelength i.e. with low size dispersion, requires highly accurate precision and perfect control over operating conditions and the synthesis process. They are therefore very difficult to produce. The wide range of colours offered by these semiconductor crystals is due to a size variation in the order of a few Angström (i.e. a few atomic layers). Syntheses in solution rarely allow such a high degree of precision to be attained. In addition, the recombination of electron-hole pairs seen on the surface of the nanocrystals limits the quantum yield to a low value.

To bypass this problem, a core/shell structure has been proposed: this entails individually coating the fluorescent semiconductor nanocrystals with a layer of semiconductor material having a wider gap (ZnS, CdS). Also, the selective labelling of biomolecules with fluorescent semiconductor nanocrystals requires the formation of a polysiloxane layer functionalized by amine groups (epoxy and carboxylic acid). These form the anchor points for the biomolecules. The preparation of these nanocrystals therefore requires at least three synthesis steps, the first two being very delicate and hence difficult to be applied at industrial level.

Labelling with oxide nanoparticles made luminescent by doping with luminescent ions (rare earth), despite promising results, is not yet very widespread. Its main shortcoming lies in its low quantum yield which requires the use of a laser to excite the luminescent ions present in the crystal matrix. Also, the luminescence properties are markedly deteriorated when these particles are directly used in an aqueous medium.

Particular mention may be made of the patent application published under number US 2003/0180780 which describes nanoparticles of metal oxide coated with silane which can be used as labelling agent for molecules of biological interest. The only example given concerns nanoparticles of $Eu_2O_3$ coated with a very thin layer of silane obtained from 3-aminopropyltrimethoxysilane (APTMS), these nanoparticles having a mean diameter of between 100 and 200 nm.

For biological applications, it is of interest to use nanoparticles of smaller size whose colloidal suspensions exhibit better stability and whose components show greater <<furtivity>> or <<molecularity>>. The use of smaller size nanoparticles for labelling allows improved targeting of biological functions.

Within this context, the present invention sets out to provide hybrid probe nanoparticles for biological labelling, of sufficiently small size and exhibiting improved stability against attack by an external aqueous medium in particular.

The subject of the invention is therefore hybrid nanoparticles containing:
- a nanosphere, of mean diameter included in the range from 2 to 9 nm, of which at least 90% by weight consists of $Ln_2O_3$ where Ln represents a rare earth, optionally doped with a rare earth or an actinide, or a mixture of rare earths, or a rare earth and actinide mixture, in which at least 50% of the metal ions are rare earth ions,
- a coating around the nanosphere chiefly consisting of functionalized polysiloxane, having a mean thickness included in the range from 0.5 to 10 mm, preferably greater than 2 nm and no more than 10 mm, and
- at least one biological ligand grafted by covalent bonding to the polysiloxane coating.

In particular, the use of nanoparticles of $Ln_2O_3$ sesquioxide doped with a rare earth is particularly advantageous, given the extreme narrowness of their emission ray and the possibility of obtaining different emission rays by doping with different cations.

In addition, the use of nanoparticles made luminescent through the presence of rare earth ions (excellent photostability, long lifetime of the excited state) in the core nanosphere, and of luminescent molecules in and/or on the surface of the coating allows time-resolved detection, in particular when a high performance tool for optic imaging is used such as time resolved luminescence microscopy.

Also, if these nanoparticles contain lanthanides having magnetic characteristics of interest, such as gadolinium, they can be used as contrasting agent for MRI or also in therapeutic systems enabling the destruction of targeted cells subsequent to the interaction of the nanoparticles with an externally applied alternating magnetic field, generating hyperthermia for example.

Further, if these nanoparticles contain elements having extensive neutron capturing capability coupled with a highly energetic reaction such as $^{157}Gd$ or $^{235}U$, they can be used for therapy (against cancer for example) based on neutron capture.

Colloidal suspensions of the above-defined nanoparticles also form part of the invention.

A further subject of the invention is a method for preparing hybrid nanoparticles such as defined above, optionally in the form of a colloidal suspension, comprising the following successive steps:
a) preparing a colloidal suspension of nanospheres, of mean diameter included in the range from 2 to 9 nm consisting, for at least 90 wt. %, of $Ln_2O_3$ where Ln represents a rare earth optionally doped with a rare earth or an actinide, or a mixture of rare earths, or a rare earth and actinide mixture in which at least 50% of the metal ions are rare earth ions,
b) adding to the colloidal suspension the necessary quantity of a mixture of organoalcoxysilane and cross-linking agent to form a coating on the surface of the particles, chiefly consisting of polysiloxane functionalized with at least one reactive group, having a mean thickness included in the range from 0.5 to 10 nm, preferably greater than 2 nm and no more than 10 nm, and
c) chemically grafting at least one biological ligand to the coating, by coupling with a reactive group present on the coating surface,
d) optionally separating and drying the hybrid nanoparticles obtained.

The description below, with reference to the appended figures, provides a better understanding of the subject of the invention. The different variants described below, when they do not exclude each other, may be combined.

As a preamble to a more precise description of the invention, the definitions of the terms used in the remainder of this disclosure are given below. The rare earths comprise scandium and yttrium and the lanthanide series which are Ce, Pr, Nd, Pm, Sm, Eu, Gd, Tb, Dy, Ho, Er, Tm, Yb, Lu. In the meaning of the invention, by rare earth is preferably meant an element chosen from among yttrium and the lanthanide series.

The actinides are Ac, Th, Pa, U, Np, Pu, Am, Cm, Bk, Cf, Es, Fm, Md, No and Lw.

The mean diameter or median diameter of the nanospheres, called $d_{50}$, is defined by the diameter below which 50% of the mass of nanospheres is found and is determined by laser diffusion technique (photon correlation spectroscopy).

A $Ln_2O_3$ sesquioxide is said to be doped by a rare earth or an actinide if the latter is present to the proportion of no more than 25% of the metal ions. Beyond this value, it becomes a mixture.

The present invention concerns a probe for biological applications essentially comprising a core nanosphere surrounded by a coating, also called a ring, enabling the grafting by covalent bonding of at least one biological ligand and optionally other organic molecules. The nanosphere is an essentially spherical, inorganic, luminescent core of nanometric size. More precisely, this spherical core consists of $Ln_2O_3$ in which Ln represents a pure rare earth, or doped with a rare earth, an actinide or a combination thereof, or a mixture of rare earths, or a rare earth and actinide mixture in which at least 50% of the metal cations are rare earth cations. This core nanosphere has a mean diameter ranging from 2 to 9 nm. At least 90% by weight of the nanosphere consists of $Ln_2O_3$ as defined above, the remainder possibly consisting of the corresponding hydroxide.

The coating is an intermediate layer surrounding the nanospheres, to which biological ligands are bound by covalent binding. The coating chiefly consists of functionalized polysiloxane and has a mean thickness ranging from 0.5 to 10 nm, preferably greater than 2 nm. The function of this coating, without this list being limitative, is at least threefold: it must ensure the protection (seal) of the core against the outside medium; it must act as grafting sites for the biological ligands bonded onto it; it must increase the optical performance of the mineral core, by energy transfer from the UV-absorbing ring towards the core re-emitting in visible wavelength.

The type of nanosphere forming the spherical core of the inventive nanoparticles is chosen in relation to the targeted application, and preferably consists of at least 80% by weight of a rare earth sesquioxide, optionally doped. Preferably, this nanosphere is doped or even co-doped i.e. doped with at least two elements of different type.

Advantageously, the nanosphere consists of at least 80% by weight, and preferably at least 90% by weight, of $Y_2O_3$ or $Gd_2O_3$, $Gd_2O_3$ being preferred.

When conventional luminescence is desired, the nanosphere is doped with a lanthanide of Eu, Tb, Er, Nd, Yb, Tm type representing from 0.1 to 25% of the metal cations of the nanosphere. When luminescence in the infra-red is desired, the nanosphere is doped with a lanthanide of type Nd or Yb. When antistokes luminescence is desired, the nanosphere is doped with a lanthanide of Er type.

As mentioned previously, for combined detection (multiplexing), the nanosphere is doped with at least two different lanthanides representing from 0.1% to 25% of the metal cations of the nanosphere, at least one of these lanthanides being chosen from among Eu and Tb.

Also, to facilitate detection, in particular for applications in the area of magnetic resonance imaging (MRI) or therapeutic applications, it is advantageous that the nanosphere, in addition to its luminescence properties, should have magnetic properties. Therefore, advantageously, the nanosphere contains rare earth cations exhibiting magnetic behaviour chosen from among Gd, Nd representing at least 10% of all the metal cations present in the core for a medical imaging application, and at least 50% for a hyperthermia application.

According to another advantageous variant, from 0.01% to 50%, preferably from 0.1 to 10% of the metal cations of the nanosphere are actinide cations chosen from among Ac, Th, Pa, Np, U, Pu. Doping the nanosphere with said radionuclides finds particular application in nuclear reaction-related therapy.

Another advantageous variant concerns hybrid nanoparticles in which at least 0.1% of the metal cations of the nanosphere are radioactive isotopes whose half-life is less than 1000 years, or in which at least 1%, preferably at least 5% of the metal cations of the nanosphere are isotopes having extensive neutron-capture capability coupled with high reaction energy (e.g. $^{157}$Gd, $^{235}$U). Said nanoparticles are of great interest for therapy systems based on nuclear decomposition reactions, e.g. for the destruction of cancer cells.

Preferably, the nanosphere consists of at least 90 wt. % lanthanide sesquioxide, optionally doped. The inventive, hybrid nanoparticles whose nanosphere consists of at least 90 wt. % $Gd_2O_3$ doped with Tb or Eu are particularly preferred. $Gd^{3+}$ is a cation which exhibits both strong paramagnetism and can act as matrix for the luminescent Eu and Tb cations.

The nanospheres of rare earth sesquioxide, in particular gadolinium sesquioxide, are sensitive to hydrolysis in an aqueous medium. To prevent the conversion of the sesquioxide into a hydroxide, it is coated with a protective layer chiefly consisting of functionalized polysiloxane. This layer must be sufficiently thick to ensure this protection: its mean thickness ranges from 0.5 to 10 nm, and is preferably more than 1 nm. The coating layer advantageously represents at least 20% of the total volume of the nanoparticle, and preferably from 25 to 75% of the total volume of the nanoparticle. The thickness is measured by laser particle size measurement (Photon Correlation Spectroscopy). It is also possible, for an isolated nanoparticle, to measure the diameter of the nanosphere and the thickness of the layer by transmission electronic microscopy.

Advantageously, this coating protects the luminescence properties of the oxide core and/or allows energy transfer in relation to the spherical core i.e. the UV excitation is absorbed by the ring of polysiloxane and transferred to the spherical core, which increases its luminescence. This function is particularly ensured if 5 to 75%, preferably 30 to 50%, of the silicon atoms of the polysiloxane layer are each bound to four other silicon atoms by oxygen bridges, which constitutes a preferred variant of the invention. Consequently, according to one advantageous variant of the invention, 25 to 95%, preferably 50 to 70%, of the silicon atoms in the functionalized polysiloxane coating are covalently bound to a carbon atom and are therefore functionalized.

Also, the density of this functionalized polysiloxane layer can be chosen in relation to the priority effect it is desired to achieve. In particular, a layer having a density ranging from 1.6 to 2.4, preferably ranging from 1.8 to 2.1, is preferred to further promote the protection of the spherical core against hydroxylation and to maintain its luminescence. Coating with a density of less than 2 is preferred for MRI or hyperthermia applications.

This functionalized polysiloxane layer also allows the grafting by covalent bonding of at least one biological ligand, and optionally of other organic molecules or polymers. In particular, between 10 and 100 000 luminescent organic molecules, chosen in particular from among the derivatives of rhodamine or fluorescein, are grafter on the surface and/or within the coating, in addition to the biological ligand or ligands, allowing time resolved detection. The lifetime of the excited state is a few nanoseconds for the luminescent organic molecules, and in the order of one microsecond for the nanoparticles of lanthanide sesquioxide.

According to one variant of the invention, 1 to 1000 and preferably 1 to 100 molecules of biological ligand are grafted onto the functionalized polysiloxane layer by covalent bonding. According to another variant of the invention, less than 10% by weight of these nanoparticles comprise more than two molecules of biological ligand grafted onto the intermediate layer.

By biological ligand, is meant a compound which has at least one recognition site enabling it to react with a target molecule of biological interest. The grafted biological ligands are, for example, derivatives of nucleotides, sugars, vitamins, hormones, biotin, streptavidin, or any other organic molecule having an interest for biological vectoring.

It is also possible that luminescent molecules or complexing molecules, other than the biological ligand(s), may be grafted onto the functionalized polysiloxane layer. Polar or charged molecules of organophosphate, quaternary amine type may also be grafted onto the intermediate layer. Another possibility is to graft, onto the polysiloxane layer, water-soluble polymer molecules having a molecular weight of less than 5000 g/mol, preferably less than 1000, such as polyethylene glycol for example or dextran.

The present invention also concerns a method for preparing hybrid nanoparticles such as defined above, optionally in colloid suspension form. This method comprises different successive steps detailed below.

The first step of the method lies in obtaining a large quantity of crystalline nanospheres of mean diameter between 2 and 9 nm, obtained with low polydispersivity and easily redispersable i.e. with no agglomerate formation. The inventive method includes the direct preparation of an isodispersed colloidal dispersion. By isodispersed dispersion is meant a dispersion whose size distribution measured under photon correlation spectroscopy is very close, i.e. for example more than 90% of the particles have a diameter lying between the mean diameter of the dispersion ±20% of the $d_{50}$ value. The more the diameter distribution is narrow, the more the system becomes isodispersed or monodispersed.

These nanoparticles are prepared using the polyol method. This <<polyol>> method consists of direct precipitation of a solid in a polyalcohol brought to a temperature generally between 130° C. and 250° C. A metal precursor is previously dissolved in the polyol (e.g. diethylene glycol) then, after the optional addition of a reagent, the solution is brought to a temperature of more than 150° C. The polyol acts as stabiliser, limits particle growth and minimises powder agglomeration.

With this method, different submicron oxide powders have already been synthesized, of which mention may be made of $CeO_2$, $Ce^{3+}$ doped $LaPO_4$ (C. Feldmann, *Advanced Materials*, 13 (2003) 101), and $Eu^{3+}$ doped $Y_2O_3$ (C. Feldmann, J. Merikhi, *Journal of Materials Science*, 38 (2003) 1731-1735). The nanospheres used in the present invention are, for example, obtained following the <<polyol>> method described in *Journal of Luminescence*, 102-103 (2003) 445-450, and *Journal of Colloid and Interface Science, doi: 10.1016/j.jcis.2003.10.031*. Without this list being limitative, the precursors used may be chlorides, nitrates or acetates. Higher g/l concentrations can therefore be obtained. Advantageously, a colloidal suspension containing between 100 mg and 100 g of nanospheres per liter of solvent is obtained.

The synthesis of the sesquioxide nanospheres is conducted for example at a temperature lower than 200° C. in a polar solvent such as a polyol of diethylene glycol type (DEG) whose strong solvating power makes it possible to control particle size. Precursors of the different metal sesquioxides which will form the nanospheres e.g. rare earth chlorides $RECl_3$ (RE:Gd, Y) and lanthanide chlorides $Ln'Cl_3$ (Ln':Eu, Tb, Er, Nd, Yb, Tm) or actinide nitrates (U) are dispersed in the diethylene glycol. The global concentration of metal ions advantageously lies between 0.1 and 0.5 M and the relative quantity of rare earth chlorides $RECl_3$ (RE:Gd, Y) and lanthanide chlorides $Ln'Cl_3$ (Ln':Eu, Tb, Er, Nd, Yb, Tm) or actinide nitrates (U) depends upon the desired doping level or the type of desired mixture. After stirring, an aqueous solution of sodium hydroxide, advantageously 1 ml, is added and the mixture heated in a silicon oil bath to 140° C. for one hour. When the compounds present are fully dissolved the solution is brought to 180° C. for 4 hours under vigorous stirring. The result is a colloidal solution of nanospheres dispersed in the DEG, that is stable for several months. Irrespective of the quantity of dopant (rare earth or actinide), the particles of nanometric size are in the form of a solid solution consisting of a single phase. The ion concentration and rate of hydrolysis (ratio of the quantity of added water to the quantity of metal ions) can be adjusted for size control. It was found that the $OH^-$ concentration must be as low as possible to prevent precipitation of hydroxides. The addition of one equivalent NaOH with respect to the number of moles of rare earth cations appears to be a good compromise; a lower quantity is characterized by a low yield (less than 30% lanthanide oxide) and a higher quantity by irreversible precipitation of hydroxides.

Consequently, in particularly preferred manner, at step a) of the method, a colloidal suspension containing between 100 mg and 100 g nanospheres per liter of solvent is prepared by dissolving rare earth and/or actinide precursors in a polar solvent, in particular a polyol of ethylene glycol type and heating to a temperature of between 130 and 250° C. in the presence of the quantity of water that is at least necessary for formation of the desired sesquioxide and optionally of a base such as NaOH at a concentration of between 0.01 and 1 mol/l of solvent.

The colloidal suspension of nanospheres obtained may optionally be purified and/or concentrated, by removing residual soluble salts and part of the polyol e.g. by evaporation under reduced pressure, or by changing the solvent e.g. by chromatography or dialysis, and controlling the quantity of water present in the solution.

In the meaning of the invention, the nanospheres of $Ln_2O_3$ are then coated with a layer of molecules capable of setting up strong, sustained interactions both with the surface of the sesquixoides and with organic molecules (fluorophors, dispersants.) and/or with biological ligands which are to be bound thereto. Also, this layer ensures protection of the nanospheres when they are dispersed in an aqueous medium, since it is generally observed that the nanospheres dissolve and/or there is a drop in luminescence intensity when these nanospheres are dispersed in water. For this reason network formers and not modifiers are used (which do not allow a cross-linked layer to be formed around the nanosphere). Network formers are compounds which, in addition to the bond or bonds they set up with the surface of the rare earth sesquioxide, are capable of reacting between themselves (by condensation reaction between closest neighbours) to form a veritable network trapping the nanosphere. These compounds are generally organoalcoxysilanes for formula $R_xSI(OR')_y$ where $y=2,3$; $x=4-y$ and R chosen so as to immobilize an active organic molecule. To obtain a dense, sturdy network $R_xSI(OR')_y$ is mixed with a cross-linking agent such as tetraethylorthosilicate (TEOS). The polysiloxane layer, also called a coating or ring, may in particular be obtained by hydrolysis-condensation of a mixture of organotrialcoxysilane, chosen from among aminopropyltriethoxysilane (APTES), glycidyloxypropyltriethoxysilane (GPTES), mercaptopropyltriethoxysilane (MPTES) and isocyanatopropyltriethoxysilane (IPTES), with a cross-linking agent such as TEOS in the presence of nanospheres of $Ln_2O_3$ sesquioxide such as previously obtained. The Si/C ratio is controlled by the quantity of cross-linking agent added, most often TEOS. The quantity of organoalcoxysilane/cross-linking agent added depends on the number of nanospheres dispersed in solution, on their size (and hence their surface area) and on the area occupied by an adsorbed molecule. The presence of a base of trimethylamine type is preferable, preferably between 0.01 and 0.1 mol/l. The use of organotrialcoxysilane allows the addition of reactive groups to the coating, which will enable the adhering of active molecules (biological ligand, fluorophors). Therefore, to allow this coupling, some of the precursors of organoalcoxysilane type in the polysiloxane layer carry reactive groups such as carboxylic, amine, aldehyde or epoxy groups. The hydrolysis-condensation of these precursors provides a functionalized layer of polysiloxane able to react with a biological ligand or any other organic molecule or polymer to be grafted. TEOS ensures cross-linking of the formed polysiloxane, in which the quantity of silicon atoms bound solely to oxygen atoms (cross-linking nodes) i.e. which are derived from TEOS only, lies between 5 and 75%, preferably between 30 and 50%.

The non-adsorbed molecules and the secondary products are generally extracted from the colloidal solution by dialysis against ethanol, water or an equivolume ethanol/water mixture.

Without being limitative, it is possible to detail a method for forming the polysiloxane coating, advantageously conducted in four phases. The first consists of adding to 5 ml $Ln_2O_3$ nanospheres, dispersed in a DEG solution containing $n_{APTES(1)}$, mol APTES such that $4<100\times n_{APTES(1)}/(n_{APTES(1)}+n_{APTES(2)}+n_{TEOS})<16$. After at least 20 minutes' agitation, $3n_{APTES(1)}$ mol of water diluted in DEG containing 0.1 M triethylamine ($Et_3N$) are added ($2^{nd}$ phase). The solution is left under agitation for one hour before adding ($3^{rd}$ phase) to the previous mixture $n_{APTES(2)}=5\ n_{APTES(1)}$ mol APTES and $n_{TEOS}$ mol of TEOS such that $5<100\times n_{TEOS}/(n_{APTES(1)}+n_{APTES(2)}+n_{TEOS})<75$. Finally, after 20 minutes, $(15n_{APTES(1)}+4n_{TEOS})$ mol water diluted in DEG containing 0.1M triethylamine ($Et_3N$) are added to the mixture. The mixture is then left under agitation for 48 hours at 20° C.<T<40° C.

In addition to the biological ligands, the coating of functionalized polysiloxane can enable the covalent grafting of luminescent organic molecules derived from fluorescein and rhodamine in particular. Functionalization by these fluorophors can be conducted in at least two different manners. The first consists of modifying molecules of organoalcoxysilane by these fluorophors before the hydrolysis reaction. For example, 5 to 30% of the organoalcoxysilane molecules, APTES in particular, added during the first or second above-mentioned phase, are previously coupled to fluorescein isothiocyanate (FTIC) by reaction between the amine function of APTES and the isothiocyanate function of FTIC. The precursors of polysiloxane thus modified are then added to a mixture of organoalcoxysilane and TEOS to form the coating ring. The second method consists of grafting the fluorophors after formation of the polysiloxane layer, by condensation between the reactive groups carried by the fluorophors and those present in the polysiloxane layer.

The biological ligands must be accessible for subsequent probe/target coupling reactions, and are therefore chemically grafted on the polysiloxane layer by conventional coupling with the reactive groups present, optionally preceded by an activation step. The reactions ensuring coupling are known and described for example in <<Bioconjugate Techniques>>, G. T. Hermanson, Academic Press, 1996 or in <<Fluorescent and Luminescent Probes for Biological Activity. A Practical Guide to Technology for Quantitative Real-Time Analysis>>, Second Edition, W. T. Mason ed., Academic Press, 1999. For example, coupling is conducted by the addition of an aqueous solution of biological ligands whose quantity is at least greater than the number of grafting sites (corresponding to the reactive groups) on the coating. If the polysiloxane layer is functionalized with amine groups, biomolecules carrying at least one —COOH function can be grafted. However, the —COOH function of the biomolecule must previously be activated with a mixture of EDC and NHS.

After grafting the biological ligands, the excess secondary products are removed by dialysis or column chromatography. This latter technique is only used when the nanoparticles are functionalized by derivatives of fluorescein. To prevent denaturing through the repetition of the grafting and purification steps, the grafting of the biological ligands is preferably conducted last.

The inventive nanoparticles find different applications. In particular their use may be cited for the detection of biomolecules (biochips), the targeting of biological substrates (MRI imaging), for the therapeutic destruction of cells or solid tumours (hyperthermia, neutron capture).

The examples below are given solely for illustration purposes and are not of a restrictive nature.

EXAMPLE 1

A colloid of $Gd_2O_3$, 5% doped with $Tb^{3+}$, is prepared by dissolving a quantity of 50 g·l$^{-1}$ salts of gadolinium and terbium chlorides in a volume of 20 ml diethylene glycol. The final particle size, confirmed by HRTEM and measured by laser particle size measurement, is 3.5 nm. The colloid is dialysed for 24 h, under heat (40° C.) and agitation in diethylene glycol.

The ratio of the volume of own diethylene glycol/volume of colloid to be dialysed is 20. Around these particles a layer of functionalized polysiloxane, thickness 5.0 nm, is synthesized by sol-gel method. In a solution containing 5.0 ml dialysed colloid ($4.53.10^{19}$ particles·l$^{-1}$), the following are dissolved: 28.4 g·l$^{-1}$ aminopropyl-triethoxysilane (APTS), 17.6 g·l$^{-1}$ tetraethyl orthosilicate (TEOS) and 13.2 ml per liter of an aqueous solution of 0.1 M triethylamine.

The reaction is conducted at 40° C. in an oil bath under agitation. It comprises several steps:
  at t=0 h addition of $m_1$ corresponding to 16% of the total mass of APTS
  at t=0.33 h hydrolysis of APTS by adding 10% of the total water volume
  at t=1.33 h addition of $m_2$ corresponding to the remaining APTS mass and the totality of TEOS.
  at t=2.33 h addition of the 90% remaining water volume
  at t=50.33 h end of synthesis.

EXAMPLE 2

A colloid of $Gd_2O_3$, 5% doped with $Tb^{3+}$, is prepared under the same conditions as in example 1.

Around these particles a layer of functionalized polysiloxane having a thickness of 8.0 nm is synthesized by sol-gel method. In a solution containing 5.0 ml dialysed colloid ($4.53.10^{19}$ particles·$l^{-1}$) the following are dissolved: 86.4 g·$l^{-1}$ APTS, 54.2 g·$l^{-1}$ TEOS and 40 ml per liter of an aqueous solution of 0.1 M triethylamine.

The coating reaction by sol-gel method was conducted under the same conditions as in example 1.

EXAMPLE 3

A colloid of $Gd_2O_3$, 5% doped with $Tb^{3+}$, is prepared under the same conditions as in example 1, corresponding to a size of 3.5 nm. Particles of size 5.7 nm and of same composition were obtained by adding, to the previously obtained colloid, an adequate quantity of salts of gadolinium and terbium chlorides.

Around these particles, a layer of functionalized polysiloxane of thickness 8 nm is synthesized by sol-gel method. In a solution containing 5.0 ml dialysed colloid ($5.66.10^{18}$ particles·$l^{-1}$) the following are dissolved; 58.1 g·$l^{-1}$ APTS, 36.4 g·$l^{-1}$ TEOS and 28.4 ml per liter of an aqueous solution of 0.1 M triethylamine.

The coating reaction by sol-gel method was conducted under the same conditions as in example 1.

EXAMPLE 4

A colloid of $Gd_2O_3$, 5% doped with $Tb^{3+}$, is prepared under the same conditions as in example 3, corresponding to a size of 5.7 nm. Particles having a size of 8 nm and of same composition were obtained by adding, to the previously obtained colloid, an adequate quantity of salts of gadolinium and terbium chlorides.

Around these particles, a layer of functionalized polysiloxane having a thickness of 3.5 nm is synthesized by sol-gel method. In a solution containing 5.0 ml dialysed colloid ($5.65.10^{18}$ particles·$l^{-1}$) the following are dissolved: 20.6 g·$l^{-1}$ APTS, 13.0 g·$l^{-1}$ TEOS and 10 ml per liter of an aqueous solution of 0.1 M triethylamine.

The coating reaction by sol-gel method was conducted under the same conditions as in example 1.

EXAMPLE 5

A colloid of $Gd_2O_3$, 5% doped with $Tb^{3+}$, is prepared under the same conditions as in example 1.

Around these particles, a layer of functionalized polysiloxane having a thickness of 5.0 nm is produced by sol-gel method. In a solution containing 2.5 ml dialysed colloid ($4.53.10^{19}$ particles·$l^{-1}$) and 2.5 ml own diethylene glycol the following are dissolved: 28.4 g·$l^{-1}$ APTS, 17.6 g·$l^{-1}$ TEOS and 13.2 ml per liter of an aqueous solution of 0.1M triethylamine.

The coating reaction by sol-gel method was conducted under the same conditions as in example 1.

EXAMPLE 6

A colloid of $Gd_2O_3$, 5% doped with Tb 3, is prepared under the same conditions as in example 1.

Around these particles, a functionalized polysiloxane layer having a thickness of 8 nm is produced by sol-gel method. In a solution containing 2.5 ml dialysed colloid ($2.26.10^{19}$ particles·$l^{-1}$) and 2.5 ml own diethylene glycol the following are dissolved; 9.4 g·$l^{-1}$ APTS, 6.4 g·$l^{-1}$ TEOS and 4.4 ml per liter of an aqueous solution of 0.1M triethylamine.

Six hours before adding mass $m_2$ of APTS the latter is mixed under magnetic stirring with 1.4 g·$l^{-1}$ fluorescein isothiocyanate, a fluorescent molecule. Subsequently the coating reaction was conducted under the same conditions as in example 1 except that mass $m_1$ of APTS is combined with the FTIC.

EXAMPLE 7

Grafting of the Oligonucleotide

A solution of 100 µM d(T)22 oligonucloetides ending in a —COOH function is added to an aqueous solution of 0.2 M EDC and 0.2 M NHS. After one hour's agitation, 500 1l of an aqueous solution of nanoparticles of gadolinium oxide coated with a layer of functionalized polysiloxane (prepared according to example I and purified by dialysis) and 100 µl of a buffer carbonate solution (0.1M; pH 11) are added to the solution containing the oligonucleotide strands. After two hours' agitation, the solution gels. After filtering through a membrane, the gel is redispersed in 2000 1l milli-Q water.

EXAMPLE 8

A colloid of $Gd_2O_3$, 1% doped with uranium, is prepared by dissolving a quantity of 50 g·$l^{-1}$ salts of gadolinium chloride and uranium nitrate in a volume of 20 ml diethylene glycol. the final size of the nanospheres, confirmed by HRTEM and measured by laser particle sizemeasurement, is 3.5 nm. The colloid is dialysed for 24 h, under heat (40° C.) and agitation in diethylene glycol. The ratio of the volume of own diethylene glycol/volume of colloid to be dialysed is 20.

Around these nanospheres a layer of functionalized polysiloxane having a thickness of 5.0 nm is synthesized by sol-gel method. In a solution containing 5.0 ml dialysed colloid ($4.53.10^{19}$ particles·$l^{-1}$) the following are dissolved: 28.4 g·$l^{-1}$ aminopropyltriethoxysilane (APTS), 17.6 g·$l^{-1}$ tetraethyl orthosilicate (TEOS) and 13.2 ml per liter of an aqueous solution of 0.1 M triethylamine.

The reaction is conducted at 40° C. in an oil bath and under agitation. It comprises several steps:
- at t=0 h addition of $m_1$ corresponding to 16% of the total mass of APTS
- at t=0.33 h hydrolysis of APTS by adding 10% of the total water volume
- at t=1.33 h addition of $m_2$ corresponding to the remaining mass of APTS and the totality of TEOS
- at t=2.33 h addition of the remaining 90% volume of water
- at t=50.33 h end of synthesis.

EXAMPLE 9

A colloid of $Gd_2O_3$, 5% doped with $Tb^{3+}$ and 5% $Eu^{3+}$ in moles, is prepared by dissolving a quantity of 50 g·$l^{-1}$ salts of gadolinium, terbium and europium chloride in a volume of 50 ml diethylene glycol (2.260 g of $GdCl_3$, $6H_2O$, 0.1273 g of $EuCl_3$, $6H_2O$ and 0.1250 g of $TbCl_3$, $6H_2O$). After adding 3 ml of an aqueous solution of 2N NaOH at 70° C., heating to 140° C. for 1 h, then at 180° C. for 4 h, the final particle size as confirmed by HRTEM and measured by laser particle size measurement is 3.5 nm. The colloid is dialysed for 24 h, under heat (40° C.) and agitation in diethylene glycol. The ratio of the volume of own diethylene glycol/volume of colloid to be dialysed is 20.

The coating reaction by sol-gel method is conducted under the same conditions as in example 1.

Figure 1:
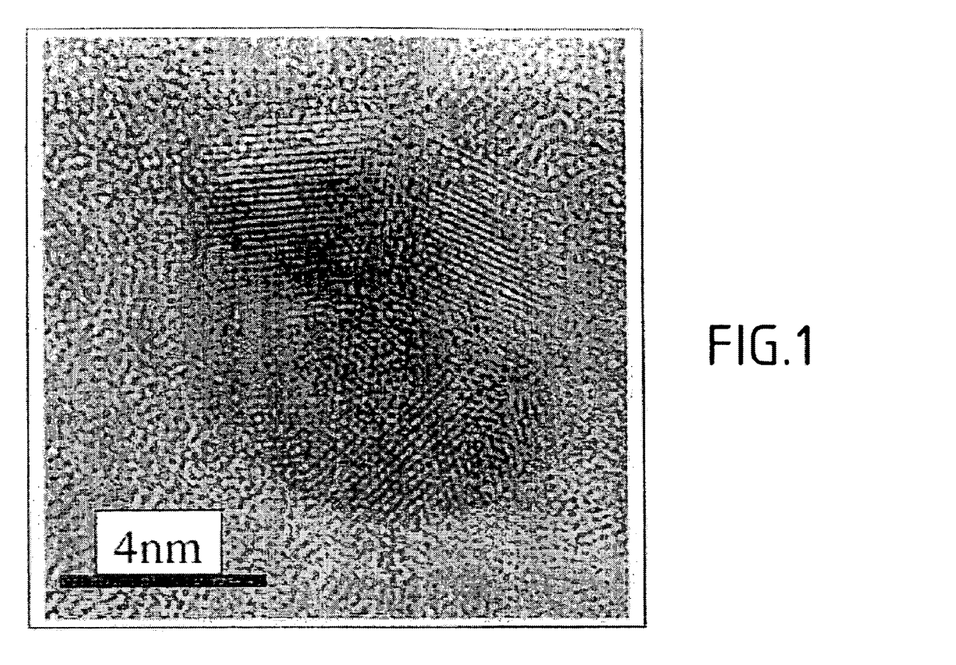
FIG. 1 is a High Resolution Transmission Electronic Microscopy view of a 8 nm particle of $Gd_2O_3:Tb^{3+}$, coated with a layer 3.5 nm thick, obtained according to example 4 below.
Figure 2:
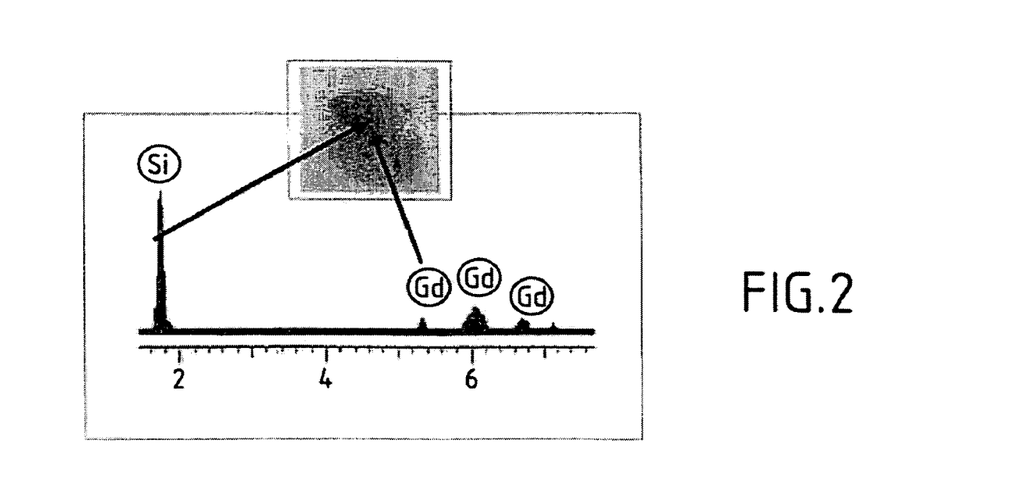
FIG. 2 is an EDX spectrum analysis (coupled to HRTEM) measured along the length of the 8 nm particle of $Gd_2O_3:Tb^{3+}$, coated with a polysiloxane layer 3.5 nm thick, obtained according to example 4 below.
Figure 3:
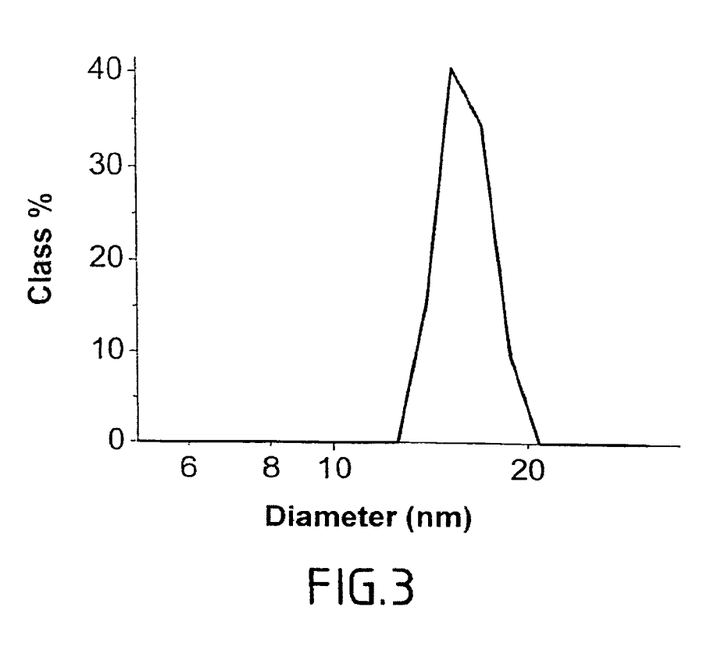
FIG. 3 gives the results of the size measurements of 8 nm particles after coating with a 3.5 nm polysiloxane layer (example 4).
Figure 4:
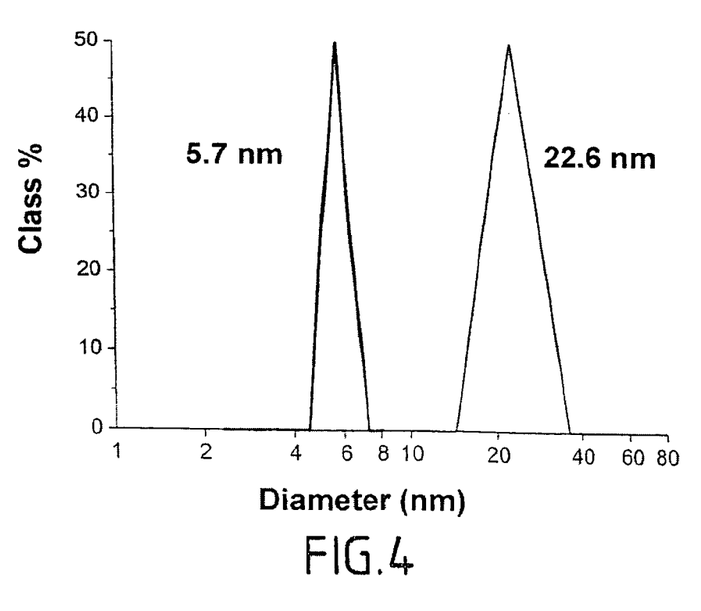
FIG. 4 gives the comparative results of size measurements of the initial particles (dialysed colloid, 5.7 nm) and after coating with a 8.0 nm polysiloxane layer (example 3).
Figure 5:
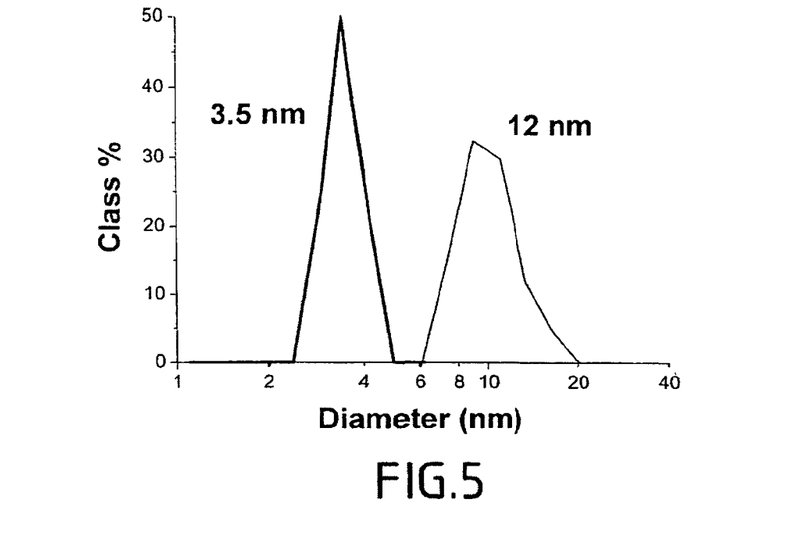
FIG. 5 gives the comparative results of size measurements of initial particles (dialysed colloid, 3.5 nm) and after coating with a 5.0 m polysiloxane layer (example 1).
Figure 6:
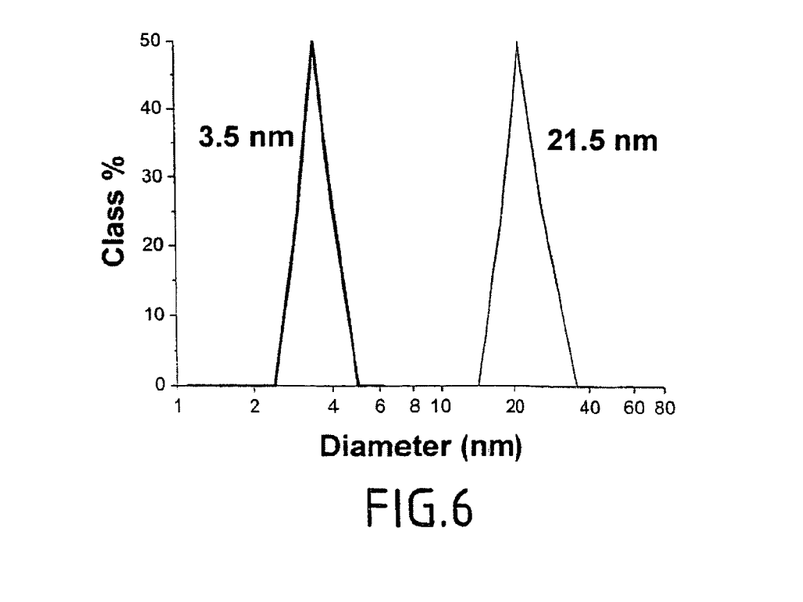
FIG. 6 gives the comparative results of size measurements of initial particles (dialysed colloid, 3.5 nm) and after coating with a polysiloxane layer functionalized with 8.0 nm fluorescein (example 6).
Figure 7:
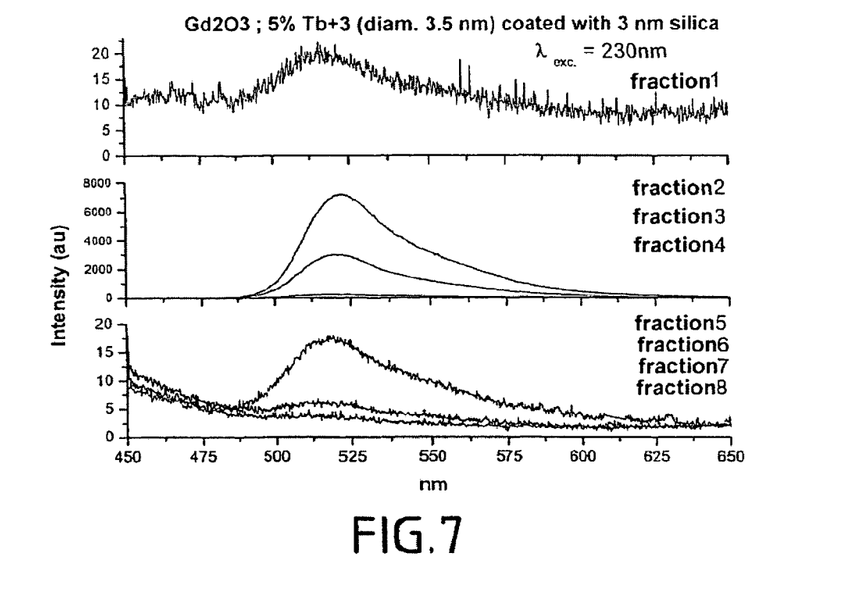
FIG. 7 shows the emission spectra of the colloid coated with polysiloxane functionalized by fluorescein as in example 6, excited at 230 nm, in relation to the different fractions obtained during column chromatography.
Figure 8:
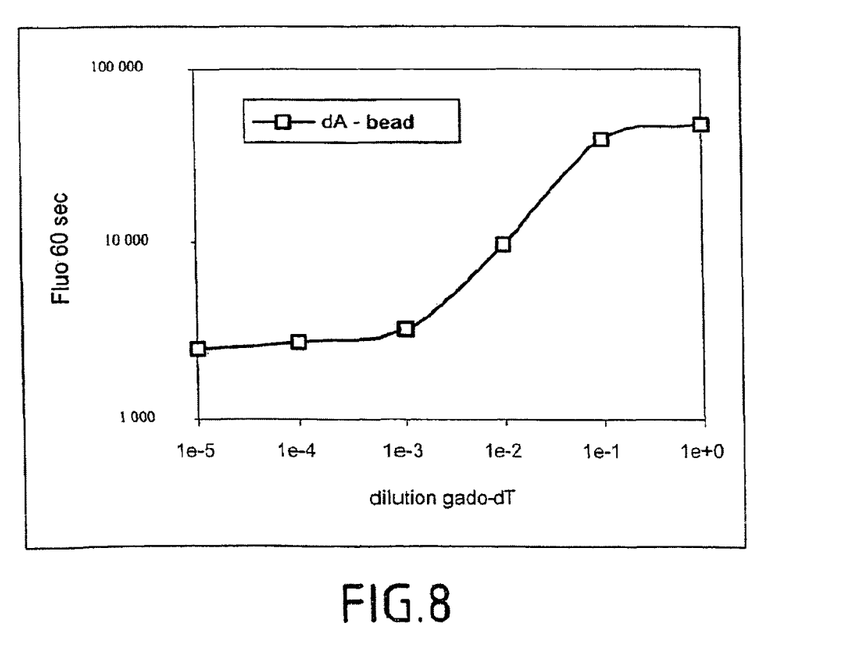
FIG. 8 shows the fluorescence of nanoparticles with gadolinium oxide core coated with polysiloxane functionalized by fluorescein and by oligonucleotide strands, these nanoparticles being immobilized on a biochip by hybridization with complementary oligonucleotide strands (example 9).
Figure 9:
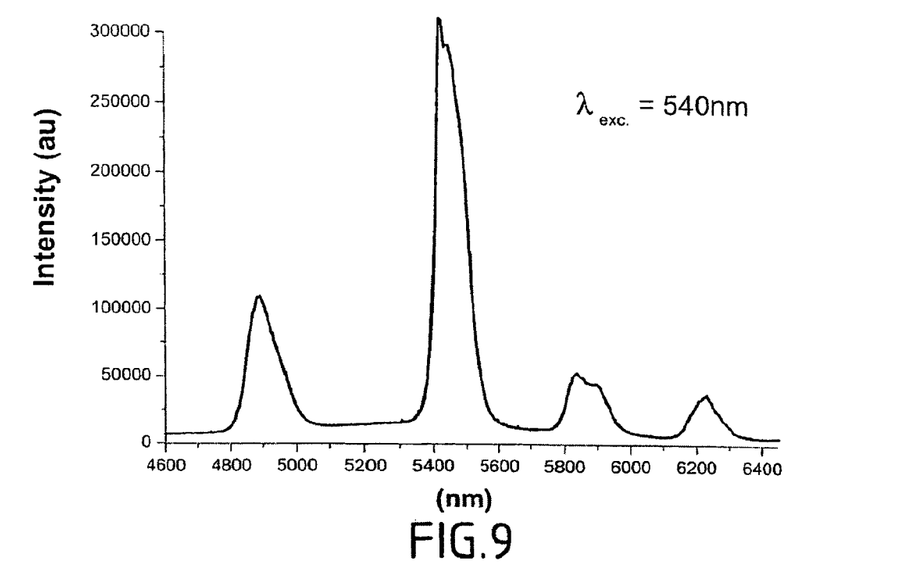
FIG. 9 shows the emission spectrum of the colloid corresponding to fraction 2 of the column chromatography shown FIG. 7, and excited at 540 nm after degradation of the fluorescein.
Figure 10:
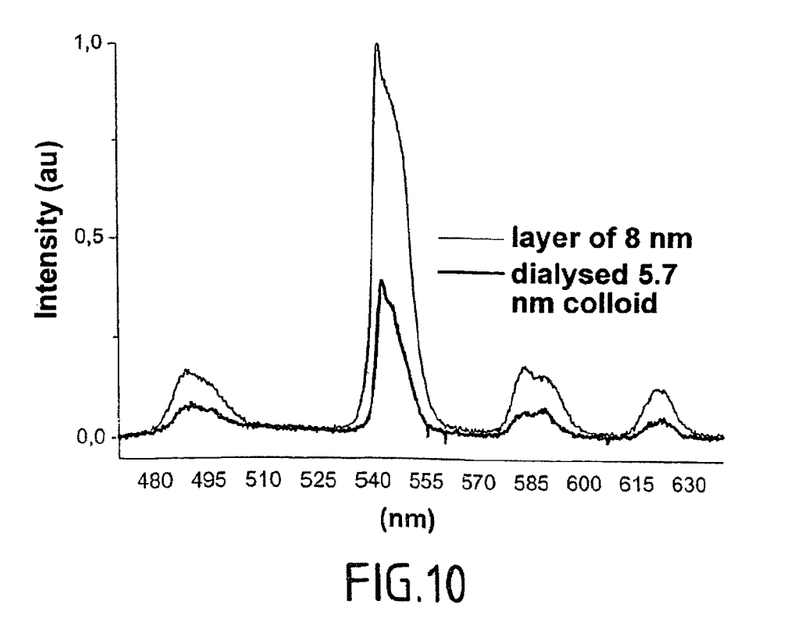
FIG. 10 gives the comparative results of luminescence measurements between the particles of initial dialysed colloid of 5.7 nm, and those coated with a 8.0 nm layer of polysiloxane (example 3).
Figure 11:
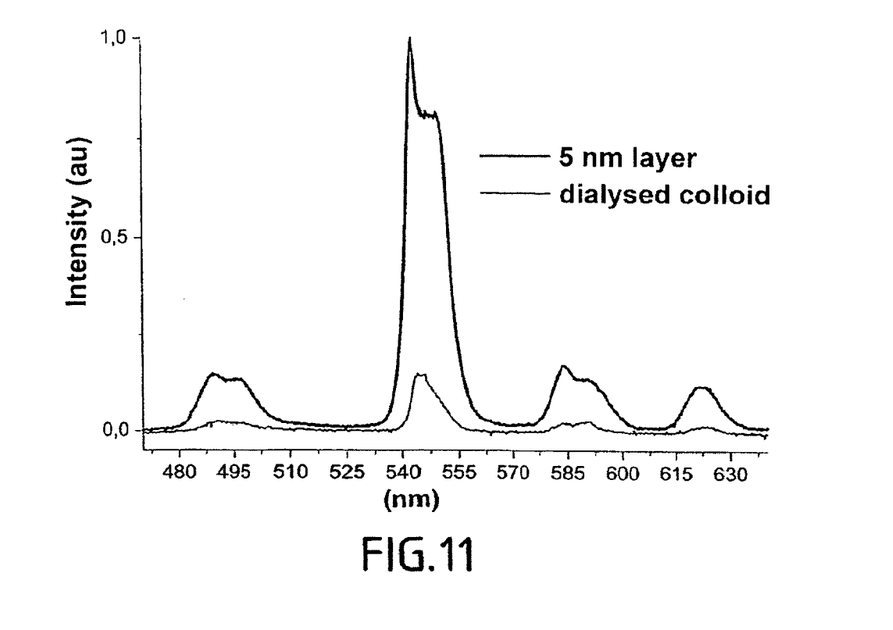
FIG. 11 gives the comparative results of luminescence measurements between the particles of the initial, dialysed colloid of 3.5 nm, and those coated with a 5.0 nm layer of polysiloxane (example 1).
Figure 12:
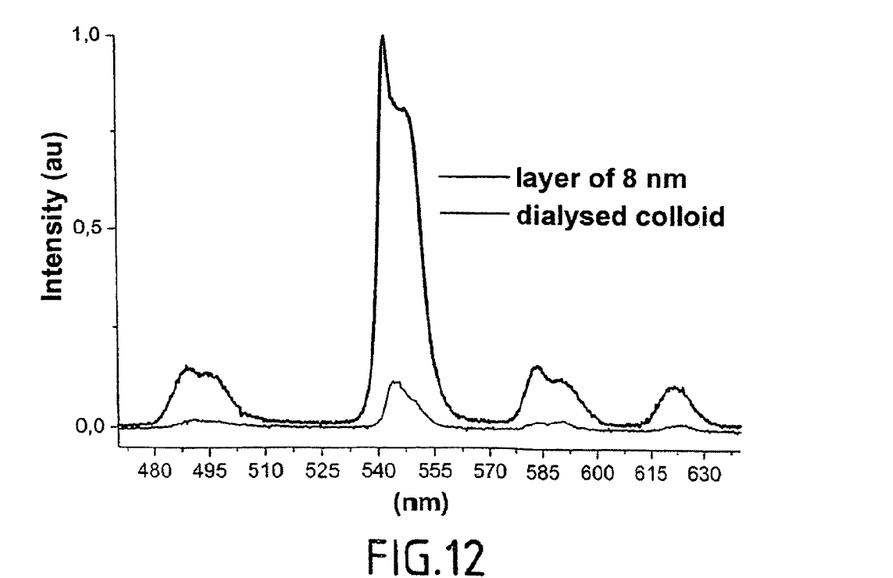
FIG. 12 gives the comparative results of luminescence measurements between the particles of the initial, dialysed colloid of 3.5 nm, and those coated with a 8.0 nm polysiloxane layer (example 2).
Figure 13:
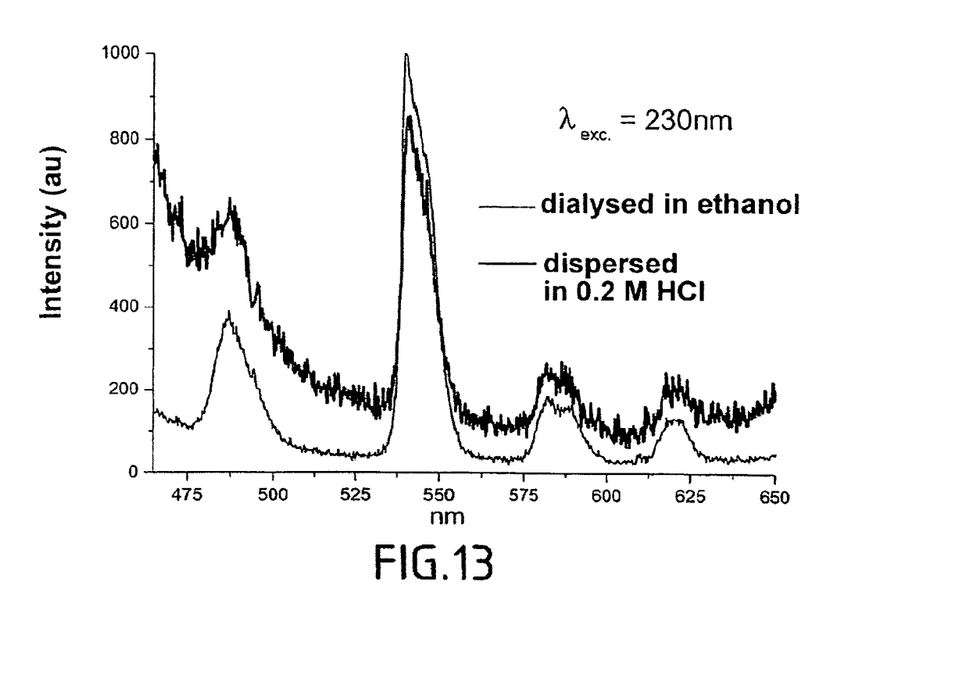
FIG. 13 shows the emission spectra of the colloid coated with polysiloxane as in example 5 excited at 230 nm, in relation to its dialysis in ethanol and its dispersion in water acidified with 0.2 M HCl.
Figure 14:
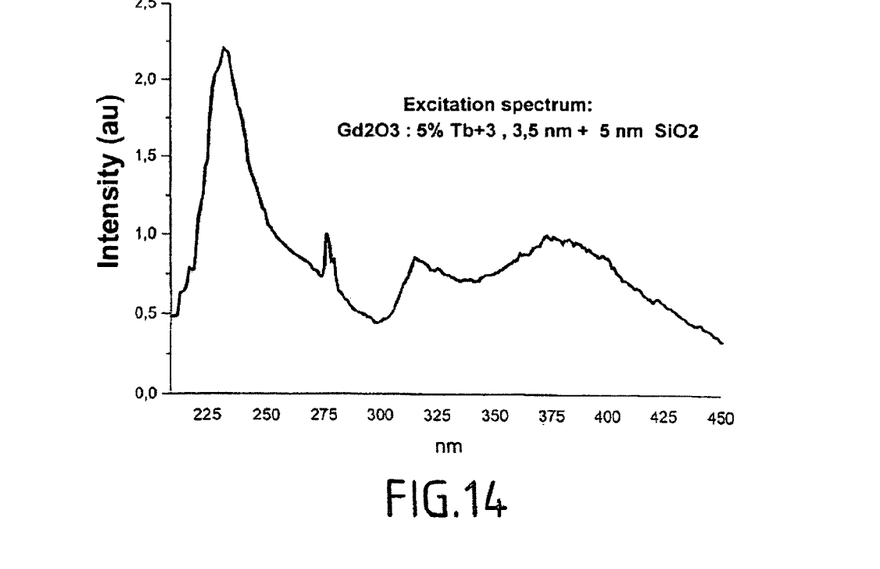
FIG. 14 shows the excitation spectrum of the particles of $Gd_2O_3$:$Tb^{3+}$ (5%) (diameter 3.5 nm) coated with a 5.0 nm layer of polysiloxane (example 1).

To test the possibility of time resolved detection (accessorily to facilitate the handling of these nanoparticles), 10% aminopropyltrialcoxysilane are functionalized with an organic dye (fluorescein) (FIG. 7). Also, its presence facilitates the purification of the hybrid nanoparticles by chromatography since its progress can easily be followed by the naked eye. Analysis of the fractions collected by UV-visible spectrophotometry and photon correlation spectroscopy confirms the visual impression and allows identification of the fractions (2 and 3 in FIG. 7) containing the hybrid nanoparticles. Chromatography is conducted using a column filled with silica gel. The volume of sample to be purified is fixed at 2.5 ml and is eluted with a aqueous solution buffered with ethanol or an equivolume water-ethanol mixture. The nanospheres of $Gd_2O_3$ doped with Tb and coated with a layer of polysiloxane, of which 10% of the amine functions are bound to a fluorescein derivative, can be used as labeller to detect biological ligands (oligonucleotides in particular). On account of the luminescence properties of terbium and fluorescein these nanoparticles, when functionalized with a probe molecule, allow the selective labelling of biological molecules on account of specific interactions with. the probes grafted on the nanoparticles, and hence their detection. In this case the grafting of an oligonucleotide modified by a carboxylic acid function onto the nanoparticle through the condensation of activated —COOH with one of the amine functions present in the polysiloxane network enables the immobilisation of the nanoparticle on a solid support if it is covered at certain points by the complementary oligonucleotide (hybridization). Subsequent to adapted electromagnetic excitation, the fluorescein emits a light signal allowing identification of the points on the support where the nanoparticle is immobilised (FIG. 8). Knowing the sequence of the oligonucleotide on the support, and by virtue of the principle of base complementarity governing the hybridization of oligonucleotide strands, the sequence of the oligonucleotide grafted on the nanoparticle can therefore be deduced. The emission of $Tb^{3+}$ ions is observed after detruction of the fluorescein by laser radiation (FIG. 9). The network of functionalized polysiloxane coating the sesquioxide nanosphere, in parallel with the grafting of active molecules, enables amplification of the luminescence signal of the dopant present in the sesquioxide core. For one same number of nanoparticles whose sesquioxide core is identical, the luminescence intensity of the $Tb^{3+}$ ions is much greater when the $Ln_2O_3$ nanosphere is coated with a layer of polysiloxane, as compared with non-coated nanospheres (FIGS. 10-12). In addition, the layer of polysiloxane ensures efficient protection against an aqueous solution of dilute hydrochloric acid. The spectra recorded from two samples containing the same quantity of identical nanoparticles, but dispersed in ethanol in one sample and the other in 0.2M HCl, show that the nanospheres coated with functionalized polysiloxane are insensitive to the presence of water (unlike uncoated nanospheres) (FIG. 13). The stability of the nanosphere in an aqueous medium and of its luminescence properties is essential in biological labelling optics. These results confirm the potential of the inventive nanoparticles, and in particular the gadolinium sesquioxide nanospheres, for the labelling and detection of biological ligands whose presence can be revealed by:
the fluorescence of organic dye molecules grafted onto the polysiloxane layer which coats the $Ln_2O_3$ nanosphere the electromagnetic radiation emitted by the dopants incorporated in the nanosphere and whose type can vary within one same nanosphere (multidoping).

magnetic measurements for nanospheres containing gadolinium sesquioxide in particular, which is paramagnetic.

The invention claimed is:

1. Hybrid nanoparticles containing:
a nanosphere, of mean diameter included in the range from 2 to 9 nm, of which at least 90% by weight consists of $Ln_2O_3$ where Ln represents a rare earth, optionally doped with a rare earth or an actinide, or a mixture of rare earths, or a rare earth and actinide mixture, in which at least 50% of the metal ions are rare earth ions,
a coating around the nanosphere chiefly consisting of functionalized polysiloxane, having a mean thickness included in the range from 0.5 to 10 nm, and
at least one biological ligand grafted by covalent bonding to the polysiloxane coating.

2. Nanoparticles as in claim 1, characterized in that in the coating from 5 to 75% of the silicon atoms are bound to four other silicon atoms by oxygen bridges.

3. Nanoparticles as in claim 1, characterized in that the coating has a density included in the range from 1.6 to 2.4.

4. Nanoparticles as in claim 1, characterized in that the coating has a density of less than 2.

5. Nanoparticles as in claim 1, characterized in that between 10 and 100 000 luminescent organic molecules are grafted, by covalent bonding, to the coating.

6. Nanoparticles as in claim 5, characterized in that the luminescent organic molecules are chosen from among the derivatives of rhodamine or fluorescein.

7. Nanoparticles as in claim 1, characterized in that the nanosphere, for at least 80% by weight, consists of a rare earth sesquioxide, optionally doped.

8. Nanoparticles as in claim 7, characterized in that the nanosphere, for at least 80% by weight, consists of $Gd_2O_3$.

9. Nanoparticles as in claim 7, characterized in that the nanosphere, for at least 80% by weight, consists of $Y_2O_3$.

10. Nanoparticles as in claim 1, characterized in that the nanosphere is doped with a lanthanide of type Eu, Tb, Er, Nd, Yb, Tm representing from 0.1 to 25% of the metal cations.

11. Nanoparticles as in claim 10, characterized in that the nanosphere is doped with a lanthanide of type Nd or Yb.

12. Nanoparticles as in claim 10, characterized in that the nanosphere is doped with a lanthanide of type Er.

13. Nanoparticles as in claim 1, characterized in that the nanosphere is doped with at least two different lanthanides representing from 0.1 to 25% of the metal cations, at least one of these lanthanides being chosen from among Eu and Tb.

14. Nanoparticles as in claim 1, characterized in that more than 10% of the metal cations of the nanosphere are lanthanide cations having magnetic behaviour, chosen from among Gd, Nd.

15. Nanoparticles as in claim 1, characterized in that more than 50% of the metal cations of the nanosphere are lanthanide cations having a magnetic behaviour chosen from among Gd, Nd.

16. Nanoparticles as in claim 1, characterized in that from 0.01% to 50% of the metal cations of the nanosphere are uranide cations chosen from among Ac, Th, Pa, Np, U, Pu.

17. Nanoparticles as in claim 1, characterized in that at least 1% of the metal cations of the nanopshere having extensive neutron-capture capability, chosen from among the isotopes $^{157}Gd$ and $^{235}U$.

18. Nanoparticles as in claim 1, characterized in that from 1 to 1000 molecules of biological ligand are grafted onto the coated by covalent bonding.

19. Nanoparticles as in claim 1, characterized in that less than 10% by weight of these nanoparticles contain more than two molecules of biological ligand grafted onto the coating.

20. Nanoparticles as in claim 1, characterized in that the grafted biological ligand or ligands are derived from nucleotides, sugars, vitamins, hormones, biotin, streptavidin, or any other organic molecule of interest for biological vectoring.

21. Nanoparticles as in claim 1, characterized in that luminescent molecules or complexing molecules other than the biological ligand(s) are grafted onto the coating.

22. Nanoparticles as in claim 1, characterized in that polar or charged molecules of organophosphate, quaternary amine types are grafted onto the coating.

23. Nanoparticles as in claim 1, characterized in that molecules of water-soluble polymers having a molecular weight of less than 5000 g/mol are grafted onto the coating.

24. Colloidal suspension of hybrid nanoparticles as in claim 1.

25. Nanoparticles as in claim 23, characterized in that the water-soluble polymers are polyethylene glycol or dextran.

26. Method for preparing hybrid nanoparticles, characterized in that it comprises the following successive steps:
   a) preparing a colloidal suspension of nanospheres, of mean diameter included in the range from 2 to 9 nm consisting, for at least 90 wt.%, of $Ln_2O_3$ where Ln represents a rare earth optionally doped with a rare earth or an actinide, or a mixture of rare earths, or a rare earth and actinide mixture in which at least 50% of the metal ions are rare earth ions,
   b) adding to the colloidal suspension the necessary quantity of a mixture of organoalcoxysilane and cross-linking agent to form a coating on the surface of the particles, chiefly consisting of polysiloxane functionalized with at least one reactive group, having a mean thickness included in the range from 0.5 to 10 nm, preferably greater than 2 nm and no more than 10 nm, and
   c) chemically grafting at least one biological ligand to the coating, by coupling with a reactive group present on the coating surface,
   d) optionally separating and drying the hybrid nanoparticles obtained.

27. Preparation method as in claim 26, characterized in that at step a) a colloidal suspension containing between 100 mg and 100 g of nanospheres per liter of solvent is prepared by dissolving precursors of rare earth and/or actinides in a polar solvent, in particular a polyol of ethyleneglycol type, and heating to a temperature of between 130 and 250° C., in the presence of the quantity of water at least necessary to form the desired sesquioxide and optionally of a base such as NaOH at a concentration of between 0.01 and 1 mol/l solvent.

28. Method as in claim 26, characterized in that the precursors of rare earth or actinides are of chloride, acetate or nitrate type.

29. Method as in claim 26, characterized in that at step b), orthosilicate tetraethyl (TEOS) is used as cross-linking agent.

30. Method as in claim 26, characterized in that part of the molecules of organoalcoxysilane used are covalently bound to a luminescent molecule.

31. Method as in claim 26, characterized in that step c) is preceded by a grafting step of luminescent molecules and/or complexing molecules and/or polar or charged molecules and/or molecules of water-soluble polymers, by coupling with a reactive group present on the coating surface.

* * * * *

UNITED STATES PATENT AND TRADEMARK OFFICE
CERTIFICATE OF CORRECTION

PATENT NO. : 8,357,545 B2  
APPLICATION NO. : 10/591465  
DATED : January 22, 2013  
INVENTOR(S) : Perriat et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1367 days.

Signed and Sealed this
First Day of September, 2015

Michelle K. Lee
*Director of the United States Patent and Trademark Office*